United States Patent [19]

Feinberg

[11] Patent Number: 4,602,641
[45] Date of Patent: Jul. 29, 1986

[54] METHOD AND APPARATUS FOR NMR DETECTION AND IMAGING OF FLOWING FLUID NUCLEI

[75] Inventor: David A. Feinberg, Berkeley, Calif.

[73] Assignee: The Regents of the University of California, Berkeley, Calif.

[21] Appl. No.: 523,060

[22] Filed: Aug. 15, 1983

[51] Int. Cl.[4] ............................................. A61B 5/05
[52] U.S. Cl. .................................. 128/653; 324/306; 324/309
[58] Field of Search ............... 128/653; 324/306, 309; 73/861.05

[56] References Cited

U.S. PATENT DOCUMENTS

| | | | |
|---|---|---|---|
| 3,551,794 | 12/1970 | Heyden et al. | 324/306 |
| 4,205,687 | 6/1980 | White et al. | 128/663 |
| 4,471,305 | 9/1984 | Crooks et al. | 324/309 |
| 4,484,138 | 11/1984 | Bottomley et al. | 324/309 |
| 4,516,582 | 5/1985 | Redington | 128/653 |
| 4,532,473 | 7/1985 | Wehrli | 324/306 |

FOREIGN PATENT DOCUMENTS 208985 3/1968 U.S.S.R. ............................ 324/306

OTHER PUBLICATIONS

Singer, "NMR Flow Imaging", Proceedings of an International Symposium on Nuclear Magnetic Resonance Imaging, Oct. 1–3, 1981, pp. 185–190.
Singer, "NMR Diffusion and Flow Measurements and an Introduction to Spin Phase Graphing", The Institute of Physics, 1978, pp. 281–291.
Lucas et al, "Measurement of Fluid Flow Profiles Using Pulsed NMR", Journal of Physics E: Scientific Instruments, vol. 10, No. 11, 1977, pp. 1150–1152.
Halbach et al, "The NMR Blood Flowmeter-Design", Med. Phys., vol. 8, No. 4, Jul./Aug. 1981, pp. 444–451.
Heinzerling, "Technological Advances in NMR Tomography", Roentgenstrahlen, vol. 49, 1983, pp. 34–41.

Primary Examiner—Edward M. Coven
Assistant Examiner—Ruth S. Smith
Attorney, Agent, or Firm—Nixon & Vanderhye

[57] ABSTRACT

A unit volume of moving nuclei is spatially tracked by successive selectively applied NMR rf nutation pulses which solicit NMR spin-echo responses from the tracked moving nuclei. For relatively fast moving nuclei, the NMR responses will come only from the successfully tracked moving nuclei. For relatively slowly moving nuclei (where some stationary nuclei in the overlap of selective excitation regions may also be excited to give NMR responses) and/or even for faster moving nuclei, controlled de-phasing/re-phasing magnetic gradients can be applied before and after a 180° rf nutation pulse so as to effectively phase-encode the spin echo response with respect to only those nuclei having velocity. The same NMR excitation/response sequence is repeated a number of times using different de-phasing/re-phasing magnetic gradients and the velocity of the nuclei may then be derived by regression analysis. A succession of such sequences is used to generate a succession of spin-echo signals having intensity and/or phase parameters which may be two-dimensionally transformed or otherwise processed to provide an NMR image of only the moving nuclei which may be quantitatively analyzed for fluid flow parameters. In the case of pulsatile fluid flows (i.e. such as with arterial blood flow in the human body) the NMR excitation/response sequences are synchronized so as to begin each repetition thereof at a predetermined portion of the pulsatile flow cycle.

30 Claims, 9 Drawing Figures

Z-AXIS BLOOD VELOCITY = SLOPE = $\theta/(\gamma G_z\, t''\tau) = V_z$

METHOD AND APPARATUS FOR NMR DETECTION AND IMAGING OF FLOWING FLUID NUCLEI

This invention is generally directed to a non-invasive NMR fluid flow detection process and apparatus which may be used to provide both qualitative and quantitative analysis of a wide range of flowing fluid parameters within an object. Techniques are provided for handling both pulsatile and non-pulsatile fluid flows. The invention is especially useful for detecting and analyzing blood flows within the veins and arteries of living bodies.

The presently preferred exemplary embodiment of this invention has been performed using an NMR imaging apparatus of the type earlier devised by Crooks et al and described by them in U.S. Pat. Nos. 4,297,637; 4,318,043; 4,471,305; and pending U.S. patent application Ser. No. 515,117, filed July 19, 1983 (now abandoned). In particular, the two-dimensional Fourier transform imaging process described in the last mentioned copending patent application is utilized in the presently preferred exemplary embodiment of my invention. Accordingly, all of these earlier patents and patent applications are considered to be related and the entire contents of each is hereby expressly incorporated by reference.

Also related are additional copending patent applications Ser. No. 515,957 filed July 21, 1983; Ser. No. 515,857 filed July 21, 1983; and Ser. No. 515,957, filed July 21, 1983 which describe various improvements to the Crooks et al method and apparatus. The entire contents of these further related applications are also hereby expressly incorporated by reference.

Although the exemplary embodiment of this invention has been found particularly useful in detecting and analyzing blood flows within the human body, it will be appreciated that the same technique may be applied to measurement of blood flows within other living bodies and/or to fluid flows generally in any inanimate or animate object susceptible to NMR imaging processes. Although, as earlier mentioned, the exemplary embodiment of the invention has been practiced using the Crooks et al apparatus and the two-dimensional Fourier transform imaging technique described by Crooks et al, it is believed that this invention will also be useful with other types of NMR imaging apparatuses and/or imaging techniques.

Most of the earlier measurements made of blood flows or hemodynamic physiology in the human body have been made using invasive catheterization to measure the time dependent distribution of X-ray opaque contrast agents. Various X-ray imaging modalities can be used for measuring tracer agents: cineangiography, digital subtraction radiography, X-ray computer tomography, positron emission tomography or standard X-ray films, etc. In general, these X-ray techniques image the distribution of radio active or iodonated contrast agents in various blood vessels, tissue compartments, etc. in an attempt to indicate the distribution of blood in which such agents are solvated. However, these techniques are far from ideal as they involve patient discomfort, significant health risk factors and provide results having only limited validity and accuracy.

Non-invasive NMR imaging techniques are now available and are becoming of increasing utility and availability. In general, most prior efforts in this field have concentrated on the ability to image relatively stationary nuclei. However, as early as 1959, it was noted that the movement of nuclei during NMR measurement sequences affected the resulting NMR spectra. Since that time, various NMR techniques have been applied to study fluid flow in plants and to study slow non-pulsatile blood flow in veins. For example, the use of NMR to measure non-pulsatile venus blood flow was perhaps first achieved by Dr. J. R. Singer. In some of his earlier work, the elapsed time required for NMR excited nuclei to move between two coil probes placed on a human arm was measured so as to deduce some limited information about blood flow within the arm structure.

There are several present day techniques for whole body NMR imaging (e.g. Crooks et al mentioned above, Damadian et al and Andrews) which provide cross-sectional images (tomographs) of nutated proton density within the body. In general, such NMR imaging techniques require the nutated nuclei to remain stationary within the body plane being imaged during a great many repetitions of an NMR excitation/response measurement sequence.

Such imaging techniques are all based upon the fact that certain nuclei (e.g. hydrogen nuclei) possess a magnetic moment which tends to align itself with a strong externally imposed steady state magnetic field about which the nuclei magnetic moments precess at the so called Larmor frequency $f_o = \gamma B_o$ where $\gamma$ is a magnetogyric ratio constant unique to a particular nuclei and/or its structural environment and where $B_o$ is the strength of the static externally imposed magnetic field.

In the Crooks et al NMR imaging technique, rf nutation pulses are selectively applied to a predetermined subvolume (e.g. a thin planar cross-section volume) by simultaneously super-imposing magnetic field gradients along various directions and thus controlling the Larmor frequency of hydrogen nuclei to be different at different locations within the body. This permits selective application of NMR excitation signals through control of the frequency spectrum of the applied rf nutation pulses. For example, if a three dimensional rectangular Cartesian coordinance system is employed, the NMR imaging apparatus may include magnetic coil structures capable of generating a desired sequence of magnetic field gradients $G_x$, $G_y$ or $G_z$ oriented along the x, y, and z axis respectively. In such a system, it is possible to selectively nutate or "flip" NMR nuclei in a thin planar volume throughout the body. Conventionally, in the Crooks et al technique, an image of the nutated nuclei in such a plane is generated by selectively exciting it with a sequence of 90° and 180° rf nutation pulses so as to generate one or more characteristic spin-echo response signals therefrom. A number of similar such NMR response signals may be elicited and combined to improve the overall signal-to-noise ratio before the spin-echo response signals are further processed (e.g. by a two-dimensional Fourier transform technique) to provide a point-by-point image of the nutated nuclei density within the selected plane. As explained in the earlier referenced Crooks et al pending applications, such a selective excitation process permits rapid multiple plane imaging since a number of such relatively short NMR excitation/response measurement sequences may be performed at different planes within a single T1 (NMR spin-lattice relaxation time) thus increasing the effectively utilized data gathering time or duty cycle.

Even though an NMR excitation/response measurement sequence is relatively short (e.g. possibly on the order of 100 milliseconds or less), blood flowing through the plane to be NMR imaged very often moves fast enough to prevent its being imaged. For example, the blood nuclei which happen to be in the plane excited with the first 90° flip pulse may already have moved substantially out of that same plane when a subsequent 180° flip pulse is applied. Under these circumstances, no spin-echo signal contribution will be elicited from these nuclei. Stated somewhat differently, the only moving blood nuclei that can be expected to produce spin-echo signals (and to thus result in contributions to the NMR cross-sectional image) are those nuclei which happen to remain within the selectively excited plane long enough to receive both the 90° and 180° nutation pulses. Accordingly, it is not surprising to note that flowing blood typically produces very little, if any, NMR response signal and the location of such flowing blood is therefore typically apparent in a conventional NMR image by the absence of any significant NMR pixel values at that location in the image.

On the other hand, as should now be appreciated, for a certain lower range of blood flow rates with respect to the thickness of the excited plane (or other shaped volumes), and with respect to the rapidity of the NMR excitation sequence, etc., there may still be some NMR signal detectable from the flowing blood. Others have previously also noted this fact and have attempted to make quantitative measurements based upon the rate at which the non-excited blood is observed to fill the volume of a blood vessel within the NMR image plane. That is, they have attempted to measure the rate at which NMR signal response is lost due to nuclei motion and thus to indirectly infer the rate of blood movement. While this technique has been somewhat successful in measuring relatively slow non-pulsatile venus blood flows (e.g. the method has been used to determine average blood velocity in jugular veins at about 2.5 cm per second), relatively faster blood flow velocities (e.g. 10 cm per second or greater) and/or pulsatile arterial blood flow measurements are apparently not possible using this prior technique.

Now, however, I have discovered NMR imaging processes which are capable of producing accurate quantitative as well as qualitative NMR imaging of moving nuclei over a very wide range of velocities and in pulsatile (e.g. arterial blood) flows as well as non-pulsatile (e.g. venus blood) flows.

The exemplary embodiment of the present invention selectively radiates different planar volumes of nuclei in the body in synchronization with the cardiac cycle so as to permit accurate measurement of hemodynamics within the mammalian body. Quantitative measurements of blood velocity, blood pressure, tissue perfusion and blood flow rates can be made directly from the rapid sequential NMR scanning of multiple planes through arteries, veins and capillary beds of organs.

For example, a first planar volume of nuclei through the body is initially excited (e.g. by a 90° rf nutation pulse) and subsequent spin-echoes are elicited from spatially offset planes (e.g. by selectively applying 180° rf nutation pulses). If the time sequence of such selective excitations and the distance between the spatially offset excited planar volumes has successfully "tracked" a unit volume of moving blood nuclei, then the magnitude of the resulting spin-echo signals emanating therefrom are used to determine blood velocity and flow rates at the predetermined and synchronized portion of the cardiac cycle. Where relatively slow moving nuclei are involved such that stationary nuclei are included in overlapping (e.g. perhaps even entirely coincident) excited planar volumes then these stationary nuclei can be expected to also provide NMR spin-echo responses which will contribute to its overall intensity. However, by using de-phasing/re-phasing magnetic gradients which rotate the net magnetization vector both before and after a 180° rf nutation pulse, the resulting spin-echo response signal has a relative phase dependent upon the velocity of moving nuclei and the magnetic gradient parameters used to achieve such phase encoding. If the gradient parameters are then changed to other known value(s) and the resulting change in measured spin-echo signal phase is noted, conventional regression analysis techniques may be utilized to deduce the velocity of the moving nuclei.

If similar velocity measurements are repeated at different times and at different positions along a given blood vessel, then measurements of pulsatile blood pressure waves along that vessel may be made.

NMR images of arterial blood flow may be made separately from images of venous blood flow by predetermining the direction of 180° pulse plane displacements.

To provide a complete two-dimensional image of a planar cross-section of moving nuclei, the NMR pulse excitation/response measurement sequence must be repeated many times (e.g. typically 128 or 256 times in the two-dimensional Fourier transformation techniques of Crooks et al).

Where pulsatile blood flow is to be detected, each of the NMR pulse excitation/response measurement sequences is synchronized so as to begin at the same relative temporal point with respect to the heart beat or cardiac cycle. Additional synchronization to the lower rate respiratory cycle may also be desired when images are to be taken in the chest or abdominal cavities. Here, a temporal reference point with respect to the lower frequency breathing cycle would be selected after which synchronization with the higher frequency cardiac cycle would be required before initiating an NMR pulse excitation/response measurement sequence.

Although the successive selective NMR excitations must move downstream with the moving blood flow to be "tracked", because a typical complete NMR excitation/response sequence is relatively short (e.g. less than 100 milliseconds) compared with typical cardiac cycle periods (on the order of 500–1000 milliseconds or so) it is possible to utilize a rapid multiple imaging technique by moving back upstream to perform subsequent NMR excitation/response sequences on another moving unit volume of blood which, because of its upstream position, will not have been subjected to earlier NMR excitation sequences.

In short, this invention provides a way to directly determine blood velocity and related blood flow parameters both quantitatively and qualitatively without the use of contrast agents, harmful ionizing radiation such as X-rays or the like. In the preferred exemplary embodiment, an NMR spin-echo sequence is utilized to quantify vector components of blood velocity (and other related flow parameters) in three-dimensional space based upon the measured phase and/or intensity of spin-echo NMR response signals.

These as well as other objects and advantages of the present invention will be better understood by carefully reading the following detailed description of the presently preferred exemplary embodiment of this invention taken in conjunction with the accompanying drawings, of which:

Figure 1:
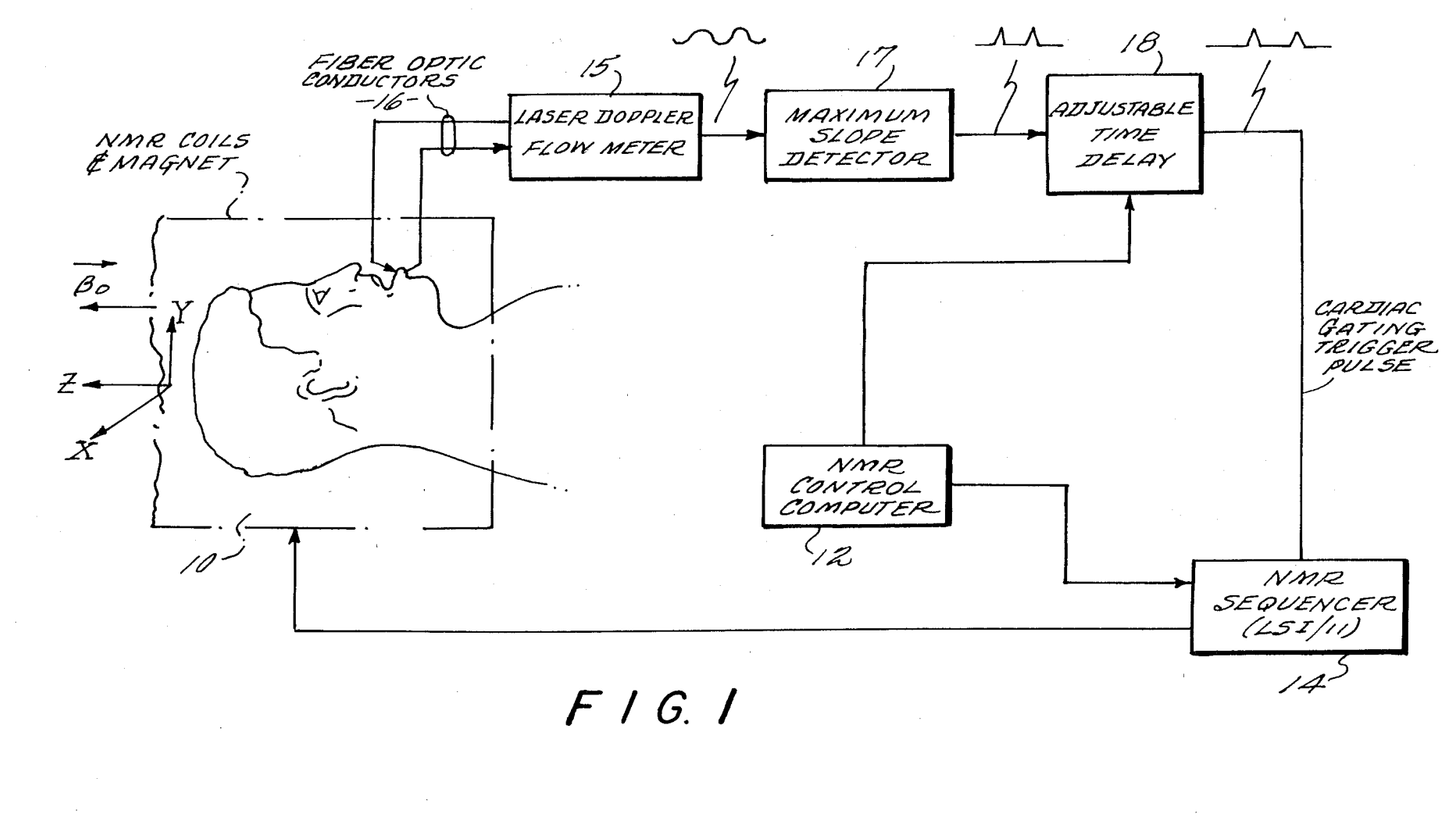
FIG. 1 is a general schematic depiction of NMR imaging apparatus which may be utilized to practice this invention.

The NMR coils and magnet structure 10 depicted at FIG. 1 may be of conventional design as may the NMR control computer 12 and NMR sequencer 14 (e.g. as described in the earlier referenced Crooks et al prior art). The hydrogen atom nuclear spins within a desired portion of a human body (e.g. the head as depicted in FIG. 1) are first aligned by a strong static magnetic field $B_o$. Then, a magnetic gradient along the z-axis is superimposed so as to make the hydrogen nuclei have differing Larmor frequencies directly proportional to their spatial position along the magnetic field gradient $G_z$. Therefore a planar volume or cross-sectional slice through the body may be selectively irradiated with rf nutation pulses having an appropriately corresponding frequency spectrum (e.g. a shaped sinc envelope of rf energy may be utilized so as to provide a substantially square shaped frequency spectrum and thus to define a planar volume having relatively sharply delineated edges). As will be appreciated, the selection of a predetermined planar volume can be changed by changing the radio frequency of the rf nutation pulse and/or by changing the magnitude of the appropriate magnetic gradient field. This process of selectively applying rf nutation pulses to only a predetermined portion of the object under test is commonly referred to as selective NMR excitation or irradiation.

Figure 2:
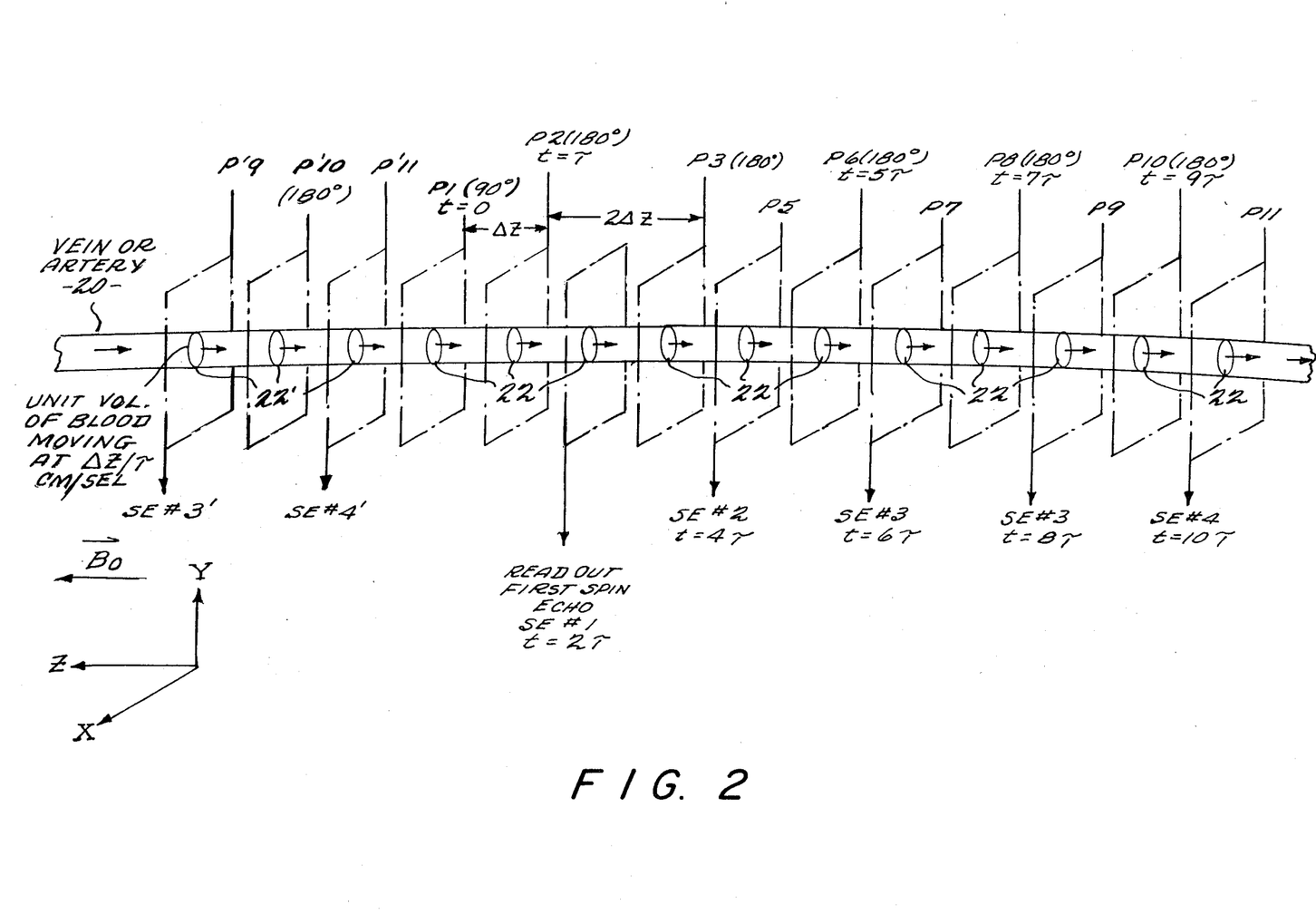
FIG. 2 is a diagrammatic depiction of an exemplary selective NMR excitation/response measurement sequence utilized to "track" a unit volume of blood flowing along a vein or artery.

A vein or artery 20 is depicted at FIG. 2 with blood flowing in the direction of the arrows. It is assumed that a unit volume 22 of this flowing blood is selectively irradiated at time $t=0$ because it happens to then be positioned within plane P1 which is at that time selectively excited with a 90° rf nutation pulse. Thereafter, at a subsequent time $t=\tau$, a second planar volume P2 (offset from the first planar volume by a distance $\Delta z$ as shown in FIG. 2) is selectively excited by a 180° rf nutation pulse. If the unit volume of blood 22 is moving at a velocity $\Delta z/\tau$, then it follows that that same unit volume 22 will be within plane P2 at $t=\tau$ and thus also be subject to the 180° nutation pulse. In accordance with the "rule of equal times", a spin echo signal will thereafter result from the excited unit volume of blood 22 at time $t=2\tau$ (corresponding to the position of plane P3 denoted in FIG. 2).

Thereafter, subsequent spin echos may similarly be elicited from the same moving unit volume of blood 22 by applying successive 180° rf nutation pulses to selected planes P4, P6, P8 and P10 at successive intervals of additional time $2\tau$ and offset distances $2\Delta z$ as depicted in FIG. 2. Of course, a given NMR sequence can only continue so long as the T2 (spin-spin relaxation time) permits further detectable spin echo signals to be elicited from a given unit volume 22. As will be appreciated by those in the art, this entire NMR excitation/-measurement sequence can be repeated numerous times within a typical spin-lattice relaxation time T1 which is often on the order of 1 second or so while the NMR measurement sequence may be on the order of only 100 milliseconds or so or less).

It will be observed that the process depicted in FIG. 2 involves the "tracking" of a unit volume of blood with selective NMR excitations. The spatial separation of the excited volumes (e.g. the planes between the 90° flip pulse and subsequent 180° flip pulses) in ratio to the elapsed time which occurs between these excitations determines the velocity of the tracked blood nuclei. The explanatory depiction in FIG. 2 has assumed the blood flow to be aligned with a single one of the applied magnetic field gradients (e.g. $G_z$). However, as will be explained in more detail, extension of this exemplary pulse sequence to other gradient directions as well as an analysis of the spin echo signal phase can be utilized to yield a complete measurement of blood flow and velocity parameters along all three orthogonal directions.

Either the time tau($\tau$) between the selectively applied NMR excitations and/or the spatial displacement $\Delta z$ between such planes may be changed so as to "track" unit volumes of blood moving at different velocities. The resulting spin echo signals may be utilized to produce NMR images of blood nuclei moving at these different velocities. In this way, it is possible to even observe the radial distribution of blood velocity within blood vessels compatible with laminar flow profiles and to confirm the existence of turbulent flow distributions (e.g. as may often be seen in the aorta during the peak velocity wave).

As will be appreciated by those in the art, the spin echo signal in this particular type of NMR excitation/-response measurement sequence is produced only by nuclei which experience both the 90° nutation pulse and the 180° nutation pulse. Therefore, if the center to center separation between the selectively irradiated planar volumes is greater than the planar volume thickness (which is determined by the frequency spectrum of the rf nutation pulses), then no stationary nuclei will be producing spin echo signals and an image of only the moving blood flow will be produced when the spin echo signals are processed to produce an image (e.g. by two-dimensional Fourier transformations or the like).

Due to movement of the nuclei during the rf nutation pulses, they may be sometimes incompletely flipped (e.g. 85° instead of 90°) thus causing isochromatic spin groups to somewhat dephase due to T1 spin-lattice decay. However, the first 180° flip pulse may have a refocussing effect on such dephased nuclei such that the second spin echo in the above-described sequence may be much greater in magnitude than the first to occur (which may not even produce a detectable spin echo signal if the dephasing effect is too great). Under these circumstances, a refocussing phasing correction gradient ($-G_z$) may be desirable immediately after the 90° or 180° nutation pulse. Its relative strength can be varied in a "tuning" process prior to the actual imaging sequence so as to find the magnitude which gives a total refocussing effect to produce the strongest spin echo signals.

Figure 3:
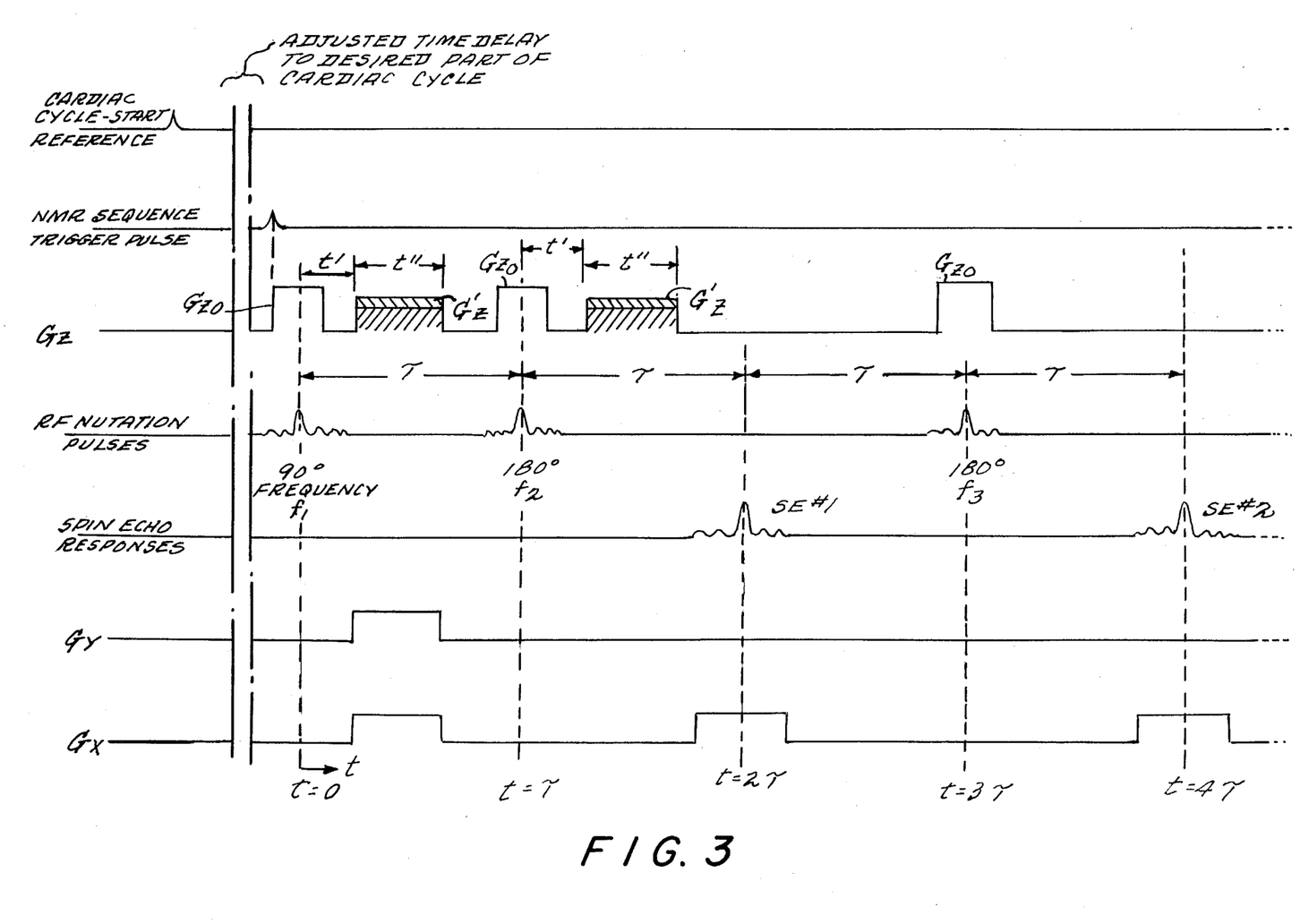
FIG. 3 is a signal timing diagram illustrating one exemplary NMR excitation/response measurement sequence useful with this information.

The NMR excitation/response sequence shown in FIG. 3 illustrates an exemplary relative timing of events. The depicted sequence is repeated many times (e.g. 128 times or 256 times for two-dimensional Fourier transformation imaging in accordance with the techniques of Crooks et al). The height of the depicted magnetic gradient pulses represents the relative strength (Gauss/centimeters) and not the shape of the gradient field which is of course a linear ramp in space. The $G_{z0}$ gradients occur concurrently with the rf nutation pulses to produce the selective planar volume excitations and, in this example, the frequency of the rf nutation pulses is varied (e.g. $f_1$, $f_2$, $f_3$, etc.) to cause the spatial movement of the selective NMR irradiation (e.g. plane P1, P2, P4, etc.). As depicted in both FIGS. 2 and 3, the resulting spin echo signals are produced in intermediate time intervals 2 tau, 4 tau, etc.

Figure 4:
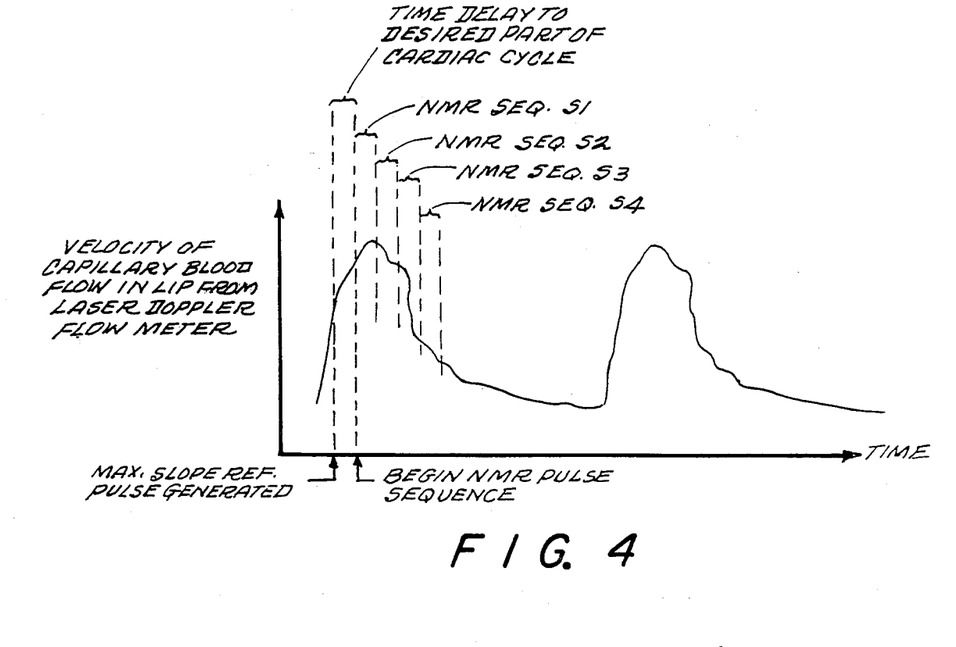
FIG. 4 is a graph useful in illustrating one way to achieve synchronization of the NMR excitation/-measurment sequence with respect to a pulsatile or cardiac cycle.

In the case of pulsatile blood flow (as is the case in the human cardiovascular system), blood velocity and instantaneous blood flow rates are periodic with respect to the cardiac cycle. FIG. 4 depicts blood velocity versus time during two successive cardiac cycles of blood flow in the descending aorta. In conventional NMR imaging of static nuclei, the NMR excitation/response sequence is repeated many times (e.g. 128 or 256 times) at random times during the cardiac cycle. Accordingly, the blood velocity has various values at different times and the resulting reconstructed NMR image typically depicts a nearly zero NMR intensity for the flowing blood.

However, in the process of this invention, where pulsatile flows are to be analyzed, the NMR excitation/response sequence is triggered or "gated" for a given NMR image only at a specific constant point in the cardiac cycle. In this way, the NMR sequence is synchronized to the cardiac cycle so as to consistently record spin echo response signals emanating from flowing blood having the same velocity.

At least three different known instruments typically used for cardiac gating in other environments (e.g. to "stop" the heart's action during computed tomographic scans and the like) are also useful in the strong magnetic field environment (e.g. 3.5 kilogauss) of an NMR whole body imager. For example, electrocardiogram signals, laser doppler flow meter signals and/or plysthagmography (pressure) signals may all be reliably and conveniently produced with conventional equipment in this strong magnetic field environment.

In the preferred exemplary embodiment, a laser doppler flow meter 15 (FIG. 1) was utilized. Dual fiber optic cables 16 were attached to the lower lip of the person being imaged and the rate of change or velocity of capillary blood flow is thus detected as shown by the waveform of FIG. 4. The earliest rising edge of the velocity signal output of the flow meter 15 is input to conventional circuitry 17 used to detect the time at which a maximum slope occurs (i.e. where the second time derivative passes downwardly through zero) to produce a sharply defined cardiac cycle/start reference signal (see FIG. 3). Any other predetermined reference point could also be used although it is desirable to produce the reference pulse as early as possible so as to permit data taking any desired subsequent portion of the cardiac cycle.

After an adjustable time delay at 18 (so as to define the desired relative time within the cardiac cycle), a cardiac gating trigger pulse is produced (see FIG. 3) to initiate a synchronized NMR excitation/response measurement cycle. Since a complete NMR sequence is relatively short compared to the usual cardiac cycle, a number of successive measurements may be made at different times within the cardiac cycle to thus increase the useful duty cycle over which the instrument may be used to gather useful imaging data. Such a succession of NMR sequences is, for example, schematically depicted at FIG. 4 with reference to the time of the cardiac cycle.

As will be appreciated by those in the art, the trigger pulse may be generated and/or utilized in various ways so as to synchronize the beginning of an NMR sequence in the fashion illustrated. For example, the output of the maximum slope detector 17 might be directly input either to the control computer or the NMR sequencer 14 which thereafter generates the desired time delay to begin an NMR sequence at a desired time within a cardiac cycle. Alternatively, the output of the adjustable time delay 18 might be input either to the control computer 12 or the NMR sequencer 14. Furthermore, a completely special purpose NMR sequencer could be constructed with each hard-wired NMR sequence being initiated only upon the occurrence of a trigger pulse. There are many possibilities.

In the preferred exemplary embodiment, the NMR sequencer 14 of Crooks et al is provided with a gating feature (e.g. so as to synchronize conventional NMR image data with the cardiac cycle and thus to obtain "stopped" images of moving heart muscle and the like) was utilized. This gating feature was earlier devised by J. C. Hoenninger, III of Crooks et al. It involves programming the NMR sequencer so as to enter a wait state just prior to initiation of an NMR excitation/response measurement sequence. The wait state is exited on the next occurrence of an input trigger pulse to thus initiate the desired NMR sequence at the desired relative time within the cardiac cycle.

When one complete NMR excitation/response sequence (for a given time within the cardiac cycle) has been completed, the NMR sequencer waits for another input trigger pulse before beginning a subsequent iteration and in this way the NMR pulse sequences are each synchronized to the cardiac cycle. By choosing various delay times, the spin echo signals (and corresponding NMR images) can be obtained at any temporal point within the cardiac cycle (e.g. as depicted at FIG. 4).

Laminar flow and pressure of incompressible fluid is described by the Navier-Stokes equations of motion for fluid, the equation of continuity for the fluid and the equation of vessel wall motion. Womersley has obtained analytical traveling wave solutions to these equations after linearization which explains pulsatile blood flows quite well, given that turbulence does not ordinarily occur within blood vessels.

Quantification of blood flow (milliliters per minute) requires measurements of blood velocity and multiplication by the cross-sectional area of the fluid flow (e.g. the illuminated or displayed portion of the blood vessel cross-section in the resulting NMR image or the blood vessel "lumen"). To measure the lumen's cross-sectional area, either a spin echo proton density image or the image resulting from use of the first spin echo signals in a sequence is used where the relatively dark low signal region of the lumen is better defined. With multiple slice spin echo images taken at 0.5 to 1 centimeter increments along the preferred axial direction, the three-dimensional orientation of the vessel in space can be determined. Accordingly, the vector components of the blood flow velocity in the axial direction can therefore be used to trigonometrically determine the blood flow velocity along the blood vessel orientation in the three-dimensional space. Similarly, a correction to the cross-sectional area of the lumen used for quantitative blood flow measurements may be made once the actual orientation of the blood vessel is determined. (That is, it is preferable to use the minimum or actual transverse cross-section of the blood vessel for quantitative measurements rather than some oblique larger cross-section area.)

The phase of spin echo signals can also be used to derive blood flow velocity measurements. For example, in the sequence shown at FIG. 3, there are extra optional magnetic gradients $G'_z$ depicted which may optionally be utilized so as to phase encode velocity data by varying their time duration $t''$ or by varying the magnitude of the gradient in two or more separate imaging sequences which each produce different phase encoded tomographs.

To understand how velocity data can be extracted from phase measurements of spin echoes, it is first necessary to understand the long-known fact that if NMR nuclei are moving during a measurement sequence, this will result in a rotation of the net nuclei magnetization vector when in the presence of a linear magnetic field gradient. That is, as has been recognized heretofore by others, the use of a phasing magnetic gradient applied to NMR nuclei (e.g. at times other than the selective application of rf nutation pulses but while the nuclei are still NMR excited) results in a phase shift of the resulting spin echo signal in accordance with the following formula:

$$\theta = \int_{t'}^{t'+t''} \gamma G_z(Z_0 + V_z t) dt \quad \text{(Equation 1)}$$

Where $Z_0$ is the initial nuclei position in the cartesian coordinate system, $V_z$ is the velocity of the nuclei in the direction of the applied magnetic gradient $G_z$ (which in this case is along the bore of the static magnet), gamma is the gyro-magnetic ratio, $G_z$ is the magnitude of the phasing gradient, t is the usual time variable and $t''$ is the elapsed time duration of the phasing gradient $G_z$.

As will thus be appreciated by those in the art, NMR nuclei will thus accumulate a phase shift proportional to the strength and to the duration of a phasing magnetic gradient such as $G'_z$ depicted in FIG. 3. This gradient is thus sometimes referred to as a "de-phasing" gradient. As will also be appreciated, the effect of a 180° rf nutation pulse is to invert the net nuclear magnetization vector so that if a similar subsequent de-phasing gradient $G'_z$ is thereafter applied, the accumulated phase shift will be in the opposite direction. Thus, this second gradient may be thought of as a "re-phasing" gradient. Accordingly, if de-phasing/re-phasing gradients having substantially the same net effect are applied both before and after a 180° nutation pulse (as is depicted by the optional cross-hatched pulses in FIG. 3), the phase encoding of stationary nuclei will be cancelled. However, the nuclei in motion will still accumulate net phase shift to provide the following accumulated phase shift in the spin echo signal (relative a fixed phase reference such as the phase of the 90° r.f. nutation pulse):

$$\theta = \gamma G_z V_z t'' \tau \quad \text{(Equation 2)}$$

Figure 5:
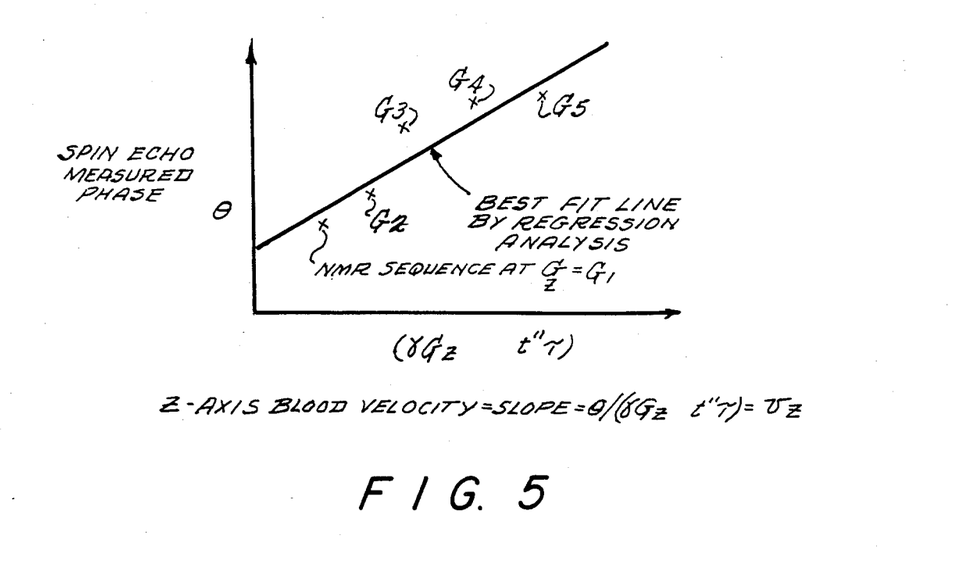
FIG. 5 is a graph illustrating a typical regression analysis technique which permits the derivation of blood flow velocity from the measured phase of successive spin-echo response signals.

By repeating this procedure two or more times using different intensities of phasing magnetic gradient or different time durations $t''$, the resulting measured spin echo relative phase values may be plotted (e.g. FIG. 5) or otherwise processed by conventional regression analysis techniques to directly determine velocity:

$$V_z = \frac{d\theta}{dG_z} (\gamma t'' \tau)^{-1} \quad \text{(Equation 3)}$$

Where $d\theta/dG_z$ is the rate-of-change of accumulated phase between the separately recorded NMR images using different values of phase-encoding parameters (i.e. magnetic gradient $G_z$ and/or elapsed time $t''$).

By using different values of $G'_z t''$ (assuming that the magnetogyric ratio gamma and the time tau between 90° and 180° flip pulses are constant parameters) the phase change $d\theta/dG_z$ varies directly with $G'_z t''$. Thus, the slope of a line fitted to a plot of $\theta$ versus $G'_z t''$ is equal to gamma, tau and the velocity along the z axis $V_z$ such that each pixel in the NMR velocity image is thus uniquely determined.

Figure 6:
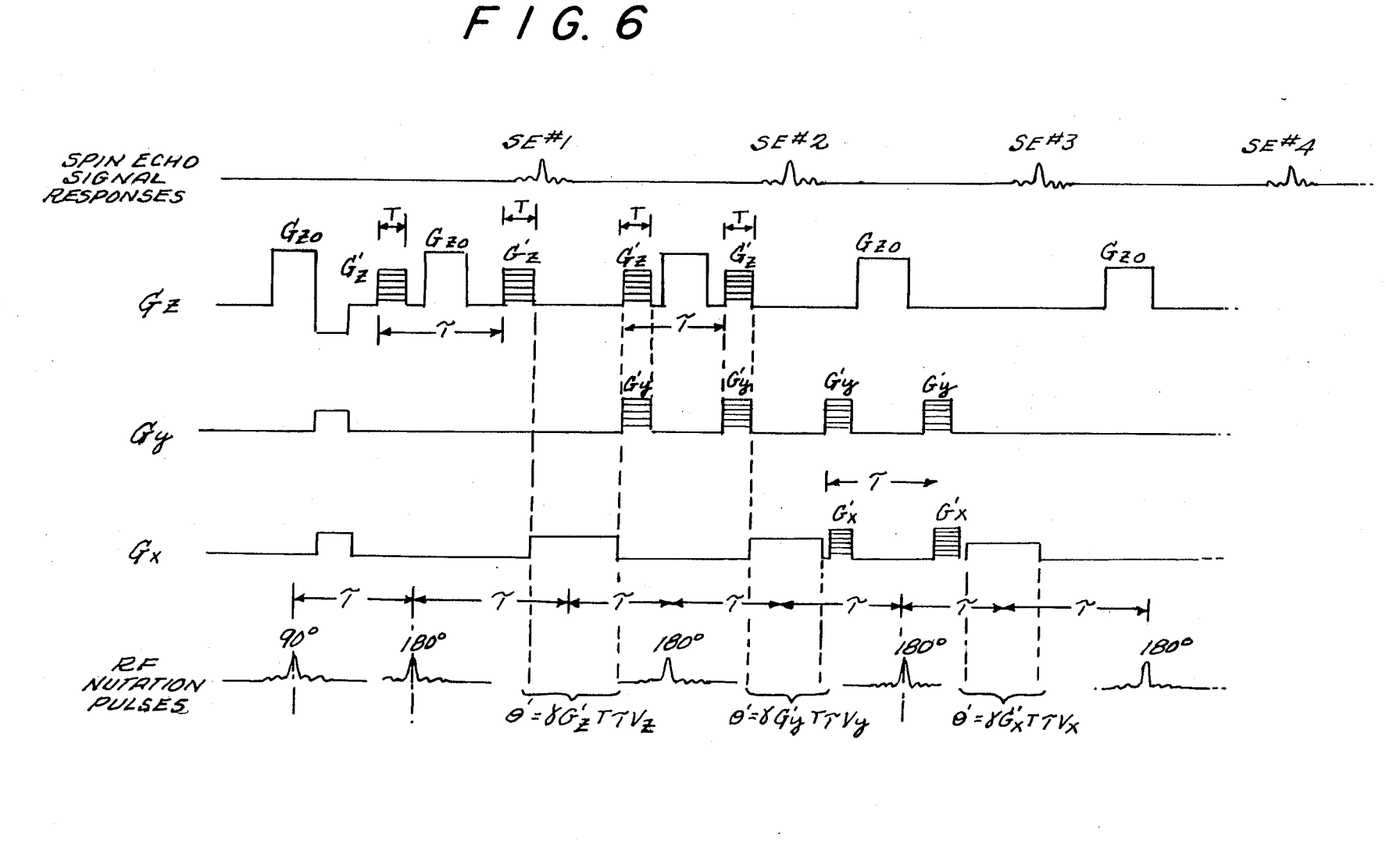
FIG. 6 is a signal/time diagram illustrating an exemplary NMR excitation/response measurement sequence for determining blood flow velocity in three-dimensions.
Figure 7:
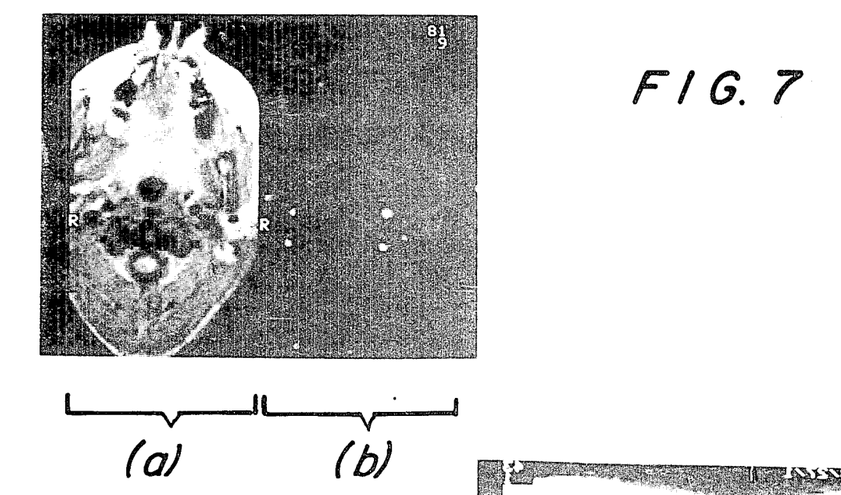
FIG. 7 illustrates a side-by-side photograph of (a) an NMR image used on a first spin echo response from a given head cross-section using overlapped 90° and 180° pulse planes showing normal head anatomy with jugular veins and internal carotids above them (dark regions) and vertebral arteries below, and (b) a similar NMR image based on a second spin echo showing only arterial blood flows in the vertebral and internal carotid arteries.
Figure 8A:
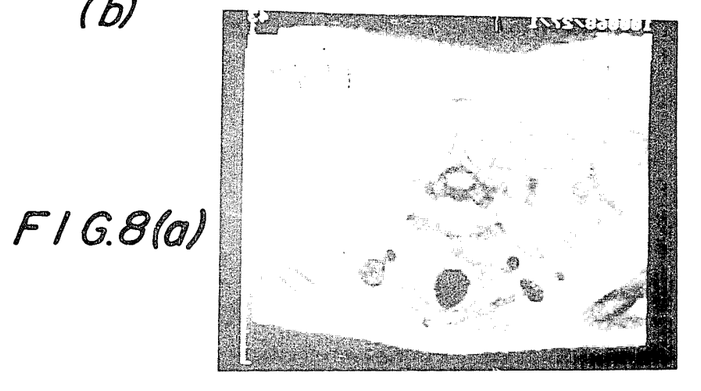
FIGS. 8a and 8b are analogous photographs showing (a) an NMR image through the neck using a first spin echo and showing neck anatomy and (b) an NMR image of that same region based on the second spin echo showing only blood flow in the venous flow direction.
Figure 8B:
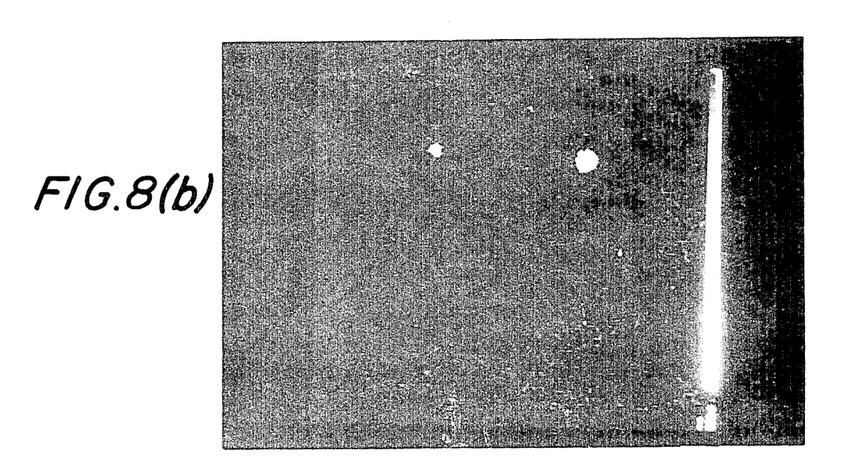

The value of $G'_z$ may be changed (for example as shown by the differently shaded areas in FIG. 3) between two or more different complete imaging sequences so as to produce two different phase-encoded velocity images. By repeatedly changing $G'_z$ for two or more NMR images, a linear regression of accumulated phase-to-gradient plot (e.g. see FIG. 5) yields the desired blood velocity measurement. Similar phase-encoding gradients can be used in the two other spatial directions ($G'_y$, and $G'_x$ as depicted in FIG. 6) to obtain velocity components in the y and x directions.

To ensure unique velocity determinations, the change in phase between two or more NMR images having detectable blood flow signals should not exceed 360° maximum. Using the maximum velocity detectable for a given pulse sequence, the range of $G'_z t''$ values can be calculated. For example, using an NMR sequence which captures a maximum blood velocity of 25 centimeters-per-second has a maximum $G'_z$ gradient value equal to $$\max G_z = (2\pi/(\gamma t'' \tau))(25 \text{ cm/sec}). \quad \text{(Equation 4)}$$

At least two different NMR images with different velocity phase encoding gradients are required to determine the velocity. An increased number of measured phase values may improve the accuracy of the resulting blood flow velocity measurement. A linear regression analysis of such phase measurements permits a more exact determination of the curve's actual slope which also represents the measured blood flow velocity.

The velocity phase encoding gradients may be applied in all three directions ($G_x$, $G_y$, and $G_z$) so as to determine the orientation of the velocity vector in three-dimensional space given that the velocity magnitude involved is detectable in the NMR images. The exemplary pulse sequence of FIG. 3 depicts the velocity phase encoding gradient only in the $G_z$ direction. At least two gradient values in each direction are needed to permit complete calculation of the velocity components in all three directions. Furthermore, a minimum of four NMR images are required so as to permit solution for the three unknowns of accumulated phase (as determined by selective irradiation gradients, read-out gradients and phase encoding gradients for a given spatial direction using two-dimensional Fourier transform techniques) and the three independent phase values in each of the three coordinate directions.

The quantification of blood velocity and blood flow can be achieved at several temporal points within the cardiac cycle by applying multislice imaging techniques (as depicted in FIG. 4). The blood pressure in arteries of the brain or other organs can then be determined from measurements of blood flow as a function of time in the cardiac cycle and position along the direction of the vessel. The multiple slice technique for measuring blood flow at different spatial and temporal points as described above can be predetermined to best fit the length and anatomy of a chosen blood vessel. Subsequently, an analysis of the blood flow images resulting from this use of predetermined parameters and also using the Navier-Stokes equation, the continuity equation for motion of blood and Hooke's law for elastic material, it is possible to derive functional expressions for the pressure-flow relationships along a segment of an artery:

$$\frac{-\partial F(z,t)}{\partial z} = C \frac{\partial P(z,t)}{\partial t} \quad \text{(Equation 5)}$$

$$\frac{-\partial P(z,t)}{\partial z} = F(z,t)R + L \frac{\partial F(z,t)}{\partial t} \quad \text{(Equation 6)}$$

Where $\mu$ is the blood viscosity, $\rho$ is blood density, $a$ is internal vessel cross-sectional area, r is the ratio of inner to outer diameter of the vessel, d is the length of the vessel segment, and E is Young's modulus of elasticity, the following values can then be found for normal blood vessels:

$$C = \frac{da}{dP} = \frac{3a(r+1)^2 d}{E(2r+1)} \quad \text{(vessel compliance)} \quad \text{(Equation 7)}$$

$$R = \frac{8\pi\mu}{a^2} \quad \text{(blood flow resistance per unit length)} \quad \text{(Equation 8)}$$

$$L = \rho/a \quad \text{(blood insertance per unit length)} \quad \text{(Equation 9)}$$

Values of $\mu$ and $\rho$, E and r can be obtained from the literature for normal blood vessels. Solving the two above differential equations using suitable conventional computer programs or otherwise, the values of pressure P can be determined from measured blood flow as a function of z and t, F(z,t). In general, this technique can be applied to NMR blood flow images in all directions and thus the blood pressure wave can be obtained from F($\bar{r}$,t) where $\bar{r}$ equals $\bar{x}$ plus $\bar{y}$ plus $\bar{z}$.

If the length of the blood vessel under investigation does not permit multi-slice imaging by repeating the 100 millisecond NMR pulse sequence during a given spin-lattice time delay T1, then fluid flow images must be recorded separately at each different desired sequential point in the cardiac cycle.

If the blood velocity is sufficiently fast, the blood volume excited by the first 90° pulse may be completely beyond the position where 180° pulses have been applied at the completion of a 100 millisecond NMR measurement interval. In such cases, then the entire 100 millisecond NMR pulse sequence can be repeated at exactly the same slice positions P1, P2, etc. (e.g. see FIG. 2).

However, there is an alternate technique for recording plural NMR pulse sequences during one cardiac cycle, each beginning with blood that has not yet been excited by any NMR. In this technique, each successive NMR pulse sequence is spatially displaced upstream while keeping the $\Delta z$ and/or frequency offset between the 90° and 180° pulses progressing in the same downstream direction as described above. Thus, each successive 90° pulse would occur further upstream where the blood flow has not yet experienced any rf excitation pulses. This technique is also depicted at FIG. 2 where the last few planes P'9, P'10, P'11, of the next NMR sequence are depicted toward the left-hand side of FIG. 2. This technique has been applied to obtain flow images of the aorta and flow images for arteries of the brain.

FIG. 6 depicts one possible combination of several velocity phase encoding gradients for determining $V_x$, $V_y$ and $V_z$ velocity components of an overall velocity vector V. By repeating the $G'_z$ gradients a third and fourth time at tau periodicity, the accumulated phase changes with respect to the z axis used for the first spin echo response are netted to zero by the time of the second spin echo response. Furthermore, concurrently with application of the third and fourth $G'_z$ pulses, $G'_y$ phase encoding pulses in the y direction are applied to yield a net phase encoding of accumulated phase with respect to the y axis in the second spin echo response. The same process of returning the accumulated phase shift along the y axis to zero (by subsequent applications of additional $G'_y$ phase correction gradients) is repeated as for the z axis so as to permit a subsequent independent measurement of the x axis velocity component which is phase encoded by a pair of $G'_x$ phase encoding gradients, one of which occurs before and one of which occurs after the third 180° rf nutation pulse as depicted in FIG. 6.

It may be necessary to only velocity phase encode the odd numbered spin echos if the tau periodic background slice-selecting gradients reduce the phase of the even numbered spin echos by returning the net phase to a near zero value. It is known by those skilled in the art that when exciting flowing nuclei within a spin echo pulse train, the odd numbered spin echos have a greater velocity dependence on phase than the even numbered echos which are to some extent rephased by the even numbered 180° rf pulses to produce nearly zero phase. It is therefore preferred that the dephasing/rephasing gradients $G'_z$ be applied immediately before and after the odd numbered 180° pulses to produce velocity phase encoded spin echos at odd numbered positions in a multi-spin echo pulse sequence. The identical $G'_z$ are subsequently applied about the even numbered 180° rf irradiations to return the nuclei phase to its original value prior to experiencing any $G'_z$ gradients. At this point, a $G'_y$ gradient is applied about the second odd numbered 180° pulse to give phase dependence of the blood vector velocity component. This process can be repeated to determine the velocity vector component in the x-direction. Determination of velocity vector components at the identical time in the cardiac cycle can be made, either by applying the gradients $G'_y$, $G'_x$ and $G'_z$ at identical times, but with different strengths in separate data acquisitions used to produce the images, or they may be applied separately at the same relative time in the cardiac cycle. Certainly, several different combinations of $G'_x$, $G'_y$ and $G'_z$ velocity encoding gradients may be found optimal for use in imaging different velocity ranges in various tissues and organs of the body in which blood flow directions are known a priori to imaging. In general, however, the velocity encoding gradients can be placed before and after any 180° rf nutation pulse and any spin echo pulse sequence to yield a direct linear dependence of phase on the corresponding velocity vector component in three-dimensional space.

To measure slow flow rates, the $G'$ vectors are also placed similar to the showing of FIGS. 3 or 6. However, in the case of slow flow rates, the spatial displacement between the successive planes of rf irradiation is reduced (perhaps to zero). In this case, by having the 90° and 180° rf nutation pulses occur in a common or overlapping spatial volume, stationary nuclei as well as slow moving blood nuclei will contribute to the spin echo response signal. Also by making the plane of 180° rf pulse several times thicker than the 90° pulse's plane on which it is centered both fast and slow flowing nuclei will produce signal. Nevertheless, application of the $G'$ gradients which phase encode only the moving NMR nuclei, will still produce information representative of nuclei velocity which is separable and independent from NMR responses emmanating from stationary nuclei. Thus, even slow capillary blood flows which slowly perfuse within tissue can be measured directly from the measured changes in accumulated phase using repeated imaging sequences with different values of phase encoding magnetic gradient parameters as described above.

The two gradients $G_z$ which phase encode the velocity of moving nuclei, are applied at times when the rf pulses are not experienced in order to give a well defined dependence of phase on velocity. The effect of a phase encoding gradient during the 90° or 180° nutating of pulses is not well defined by equation 1. However, empirical calibration of the phase-velocity relationship to gradients applied during rf irradiation may yield quantification of blood velocity from phase. Similarly, using two or more stepped gradients in separate data acquisitions as described here may yield quantification of blood velocity from phase.

It should also be noted that time-velocity curves at single positions or levels within blood vessels or tissue can be obtained by changing the time delay of the gating pulse during repeated multiple slice procedures.

In one exemplary use of the invention, a planar volume 7 mm thick was selectively excited by a radiofrequency pulse to nutate the net nuclei magnetization vector by 90°. At a time of tau=14 milliseconds later, a second planar volume, 3 mm downstream from the 90° pulse plane, was selectively irradiated by a 180° pulse thus producing a spin echo response at time 2 tau. At time 3 tau (and a position 9 mm downstream) a second 180° pulse selectively irradiated a third planar volume to produce a second spin-echo image at time 5 tau. The average velocity of nuclei producing the second spin echo response, 21.5 cm/sec., is the same as the velocity of nuclei producing the first spin echo. Additional echoes at this same velocity range can be produced from a spin echo pulse train using 180° pulses at time $\tau(2n-1)$ and position $\Delta Z(2n-1)$ where n is the number of 180° pulses and spin echo images.

Both the time, tau, (tau $=\tau$ in equation 2 and 3 and illustrations) and the distance between the planes of selective excitation can be varied to predetermine the images' velocity range. The intensity of the signal is directly proportional to the number of nuclei which happen to be moving at the tracked velocity, up to the velocity at which the magnetically excited blood volume begins to move beyond the plane of the second 180° pulse at time 3 tau. As the separation between planes of selective irradiation increases, so does the relative NMR signal intensity (e.g. up to 12 millimeter separation) for the moving nuclei as compared to stationary nuclei.

A spatial displacement in the direction of arterial flow was used to produce the images of blood flow in the human head. A first spin echo image obtained using a 4 mm overlap between the 90° and 180° planes also reveals normal brain anatomy from the stationary nuclei found in this overlapped region. The internal carotid arteries, jugular veins and vertebral arteries were also well delineated. An image derived from the second spin echo magnitude depicts only blood moving at velocity between about 5 and 21 cm/sec since stationary nuclei will not experience the second still further displaced 180° pulse.

The blood flow rates (milliliters per minute) can be determined directly in each image by integrating the velocities over the area of the vessel lumen. The flow rate per cardiac cycle, can be determined by an additional integration over all images taken during the time of a single heart beat. Improvements in accuracy of measurement can be made by taking repeated sets of images at different displacements between pulses, and similarly velocities less than 10 cm/sec. can be accurately measured using a cardiac gated pulse sequence without a displacement between the planes of excitation.

Applications of the invention to study blood flow in the vertebral, internal carotid, aorta, and femoral arteries have demonstrated its high sensitivity to laminar, pulsatile and turbulent flow. For example, in an Experiment 1, four normal volunteers were images for arterial blood flow in the head using a five slice sequence. In all of the people, a time lag between the time of peak blood velocity of the left and right internal carotid arteries was demonstrated. One possible explanation is that a higher systolic pulse wave traveled quicker in the left vessel, which is fed directly from the aortic arch, unlike the right internal carotid artery which is a branch of the brachiocephalic artery. The blood flowing to the right internal carotid likely experiences greater impedance changes due to these additional bifurcations and also travels several millimeters more than the blood in the left internal carotid before reaching the level of the NMR images.

In an Experiment 2, the venous flow was measured in a 44 year old man with atherosclerosis who had a left carotid endarterectomy 1½ years prior to imaging. The left jugular vein was found to have a blood velocity of 20 cm/sec. except in the center of the vessel where the velocity exceeded the range of the image. The right jugular's blood velocity was found to be less than that of left artery, except in the center of the vein. The corresponding phase image of the jugular veins revealed radial dependence on velocity which is compatible with laminar flow distribution. A sequence of NMR velocity images reveals concentric rings of velocity dependent phase with the maximum velocity (blue) of the right vessel equal to the slower velocity in the left jugular vein.

In an Experiment 3, the descending aorta was imaged in three normal people. In magnitude spin echo NMR velocity images, the velocity was observed to be neither radially symmetric nor constant across the vessel diameter. Such a velocity distribution is compatible with turbulent blood flow. Rapid time sequences of NMR images of the aorta, carotid arteries or other blood vessels which show pulsatile velocity changes as a function of position in the vessel and of time in the cardiac cycle yield information on the pressure pulse waves, as described above.

NMR images of blood flow can be obtained using this invention anywhere in the body in a non-invasive and safe manner since X-rays and other sources of ionizing radiation are not required. All blood velocity components in three-dimensional space can be measured. Studies to date appear to demonstrate that synchronization of the NMR pulse sequence to the cardiac cycle must be used to produce physically meaningful images of pulsatile blood flow. Application of these methods for accurate NMR hemodynamic measurements of pulse pressure, velocity, flow, and tissue perfusion can serve to further basic knowledge of human physiology in normal and diseased states, as well as offer new diagnostic procedures.

While only a few exemplary embodiments of this invention have been described in detail, those skilled in the art will appreciate that there are many possible variations and modifications that may be made in the exemplary embodiments while still retaining many of the novel advantages of this invention. Accordingly, all such modifications and variations are intended to be included within the scope of the following appended claims.

What is claimed is:

1. An NMR method for imaging flowing fluid nuclei, said method comprising the steps of:
   exciting flowing nuclei to produce an NMR response signal by applying successive slice selective NMR excitation signals to the flowing nuclei at corresponding successive spatial locations of the moving nuclei;
   detecting the resulting NMR response signal and measuring at least one of its signal parameters which is representative of nuclei velocity; and
   generating an NMR velocity image of the flowing nuclei using said measured signal parameter.

2. An NMR method as in claim 1 wherein said measured signal parameter is the intensity of an NMR spin echo signal.

3. An NMR method as in claim 1 wherein said measured signal parameter is the phase of an NMR spin echo signal.

4. An NMR method as in claim 1, 2 or 3 wherein said flowing nuclei are part of a pulsatile fluid flow and further comprising the step of synchronizing said exciting and detecting steps with respect to a predetermined temporal portion of a cycle of said pulsatile fluid flow.

5. A method for NMR detection of plusatile fluid flow velocity, said method comprising the steps of:
   (a) generating a trigger signal synchronized to a predetermined temporal portion of said pulsatile fluid flow;
   (b) in synchronization with said trigger signal, exciting to NMR signal response a selected and tracked subvolume of moving nuclei contained within said fluid flow;
   (c) detecting said NMR signal response;
   (d) measuring a predetermined NMR signal response parameter representative of the velocity of said moving nuclei; and
   (e) repeating said steps (a)-(d) to accumulate said measurements of the predetermined NMR signal response parameter and to thus generate quantitative measurements of the pulsatile fluid flow.

6. A method as in claim 5 wherein said quantitative measurements include the and the flowing fluid pressure.

7. A method as in claim 5 wherein said NMR signal response parameter comprises the intensity of an NMR spin echo signal.

8. A method as in claim 5 wherein phase-encoding magnetic gradients are employed in step (b) and wherein said NMR signal response parameter comprises the rate of change of the relative phase of the NMR spin echo signal with respect to changed phase-encoding magnetic gradients used in step (b).

9. An NMR method of detecting nuclei flowing within an object in a given direction, said method comprising the steps of:
   selectively nutating by 90° NMR nuclei then located at a first location within the object a first time;
   selectively nutating by 180° NMR nuclei then located at a second location disposed in said given direction from said first location within the object at a second time, said displacement and second time being chosen to track the movement of said NMR nuclei from said first location at a predetermined rate of movement; and
   thereafter detecting an NMR spin echo signal emanating from the NMR flowing nuclei thus selectively nutated in succession by said 90° and said 180°.

10. An NMR method as in claim 9 wherein said detecting step occurs after an elapsed time from said 180° nutation step that is approximately equal to the elapsed time between said 90° and said 180° nutation steps.

11. An NMR method as in claim 9 wherein said step of selectively nutating by 180° is successively repeated n times at locations successively displaced in said given direction by $(2n-1)$ distance units from said first location at respective time $t=(2n-1)$ time units and wherein said step of detecting an NMR spin echo signal is successively performed at times $t=2n$ time units.

12. An NMR method as in claim 9 further comprising the steps of:
   selectively applying a first predetermined phase-encoding magnetic gradient G along said given direction both before and after said step of nutating by 180°;
   measuring the resulting phase of the detected NMR spin echo signal;
   repeating all the above steps using a second predetermined phase-encoding magnetic gradient G' along said given direction; and measuring nuclei velocity in said given direction utilizing the detected change in said measured NMR spin echo phase as a function of the change between said first and second phase-encoding magnetic gradients.

13. An NMR method as in claim 9, 10, 11 or 12 used for detecting nuclei contained in pulsatile fluid flows and further comprising the steps of:
  detecting a predetermined reference time in the pulsatile fluid flow cycle; and
  synchronizing the initiation of a given sequence of all other of said steps with said detected reference time.

14. A non-invasive NMR method of measuring blood flow velocity within a living body, said method comprising the steps of:
  (a) selectively exciting nuclei of the body to NMR by applying successive excitation signals within a planar volume which spatially tracks the movements of blood nuclei flowing in a predetermined velocity range; and
  (b) detecting and quantitatively measuring an NMR response signal from nuclei which remain disposed within said planar volume throughout step (a).

15. A non-invasive NMR method as in claim 14 wherein step (a) comprises the selective application to the body of at least one 90° rf nutation pulse followed by the selective application to the body of at least one 180° rf nutation pulse.

16. A non-invasive NMR method as in claim 15 wherein step (a) comprises:
  (a1) selectively applying a 90° rf nutation pulse to the body at a time t=0;
  (a2) applying to said body a phase-encoding magnetic gradient along a first axis of intensity G for a time duration T having a phase encoding effect GT;
  (a3) selectively applying a 180° rf nutation pulse to the body at a subsequent time t=tau; and
  (a4) re-applying to said body a phase-encoding magnetic gradient along said first axis also of phase-encoding effect GT.

17. A non-invasive NMR method as in claim 16 wherein said steps (a1)–(a4) and (b) are repeated using a phase-encoding magnetic gradient along said first axis of different phase encoding effect (GT)' and wherein said detecting and measuring step (b) includes measuring the resulting relative phases of detected NMR spin echo signals occurring at t=2 tau.

18. A non-invasive NMR method as in claim 17 wherein said step (a) further comprises:
  (a5) selectively applying at least one further 180° rf nutation pulse to the body at a subsequent time to elicit at least one further NMR spin echo from the tracked flowing nuclei at a subsequent time.

19. A non-invasive NMR method as in claim 18 wherein said step (a) further comprises:
  (a6) applying to said body further phase-encoding magnetic gradients along said first axis before and after one of said further 180° pulses to cancel the phase-encoding effect along said first axis in NMR spin echoes occurring thereafter; and
  (a7) applying to said body a phase-encoding magnetic gradient along a second axis having a predetermined phase-encoding effect before and after one of said further 180° pulses to produce a subsequent NMR spin echo signal phase-encoded with respect to said second axis.

20. A non-invasive NMR method as in claim 19 wherein said step (a) further comprises:
  (a8) applying to said body further phase-encoding magnetic gradients along said second axis before and after a subsequent one of said further 180° pulses to cancel the phase-encoding effect along said second axis in NMR spin echoes occurring thereafter; and
  (a9) applying to said body a phase-encoding magnetic gradient along a third axis having a predetermined phase-encoding effect before and after a still subsequent one of said further 180° pulses to produce a still subsequent NMR spin echo signal phase-encoded with respect to said third axis.

21. A non-invasive NMR method as in claim 15 wherein said detecting and measuring step (b) includes measuring the intensity of a detected NMR spin echo signal.

22. A non-invasive NMR method as in claim 14, 15, 16, 17 or 21 further comprising an initial step of synchronizing each initiation of step (a) with a predetermined time in the pulsatile blood flow cycle of the body.

23. An NMR apparatus for imaging flowing fluid nuclei, said apparatus comprising:
  means for exciting flowing nuclei to produce an NMR response signal by applying successive slice selective NMR excitation signals to the flowing nuclei at corresponding successive spatial locations of the moving nuclei;
  means for detecting the resulting NMR response signal and measuring at least one of its signal parameters which is representative of nuclei velocity; and
  means for generating an NMR velocity image of the flowing nuclei using said measured signal parameter.

24. A NMR apparatus as in claim 23 wherein said flowing nuclei are part of a pulsatile fluid flow and further comprising means for synchronizing said means for exciting and means for detecting with respect to a predetermined temporal portion of a cycle of said pulsatile fluid flow.

25. Apparatus for NMR detection of pulsatile fluid flow velocity, said apparatus comprising:
  (a) means for generating a trigger signal synchronized to a predetermined temporal portion of a pulsatile fluid flow; and
  (b) means for repetitively exciting to NMR signal response a selected and tracked subvolume of moving nuclei contained within said fluid flow in synchronization with said trigger signal, for detecting said NMR signal response, for measuring a predetermined NMR signal response parameter representative of the velocity of said moving nuclei and to accumulate said measurements of the predetermined NMR signal response parameter and to thus generate quantitative measurements of the pulsatile fluid flow.

26. An NMR apparatus for detecting nuclei flowing within an object in a given direction, said apparatus comprising:
  means for selectively nutating by 90° NMR nuclei then located at a first location within the object at a first time;
  means for selectively nutating by 180° NMR nuclei then located at a second location displaced in said given direction from said first location within the object at a second time, said displacement and second time being chosen to track the movement of said NMR nuclei from said first location; and means for thereafter detecting an NMR spin echo signal emanating from the NMR flowing nuclei thus selectively nutated in succession by said 90° and said 180°.

27. An NMR apparatus as in claim 26 further comprising:

means for selectively applying a first predetermined phase-encoding magnetic gradient G along said given direction both before and after said step of nutating by 180°; and means for measuring the resulting phase of the detected NMR spin echo signal, for using a second predetermined phase-encoding magnetic gradient G' along said given direction during further selective NMR nutations, and for measuring nuclei velocity in said given direction utilizing the detected change in said measured NMR spin echo phase as a function of the change between said first and second phase-encoding magnetic gradients.

28. An NMR apparatus as in claim 26 or 27 used for detecting nuclei contained in pulsatile fluid flows and further comprising:

means for detecting a predetermined reference time in the pulsatile fluid flow cycle; and means for synchronizing the initiation of a given sequence of all other of said steps with said detected reference time.

29. A non-invasive NMR apparatus for measuring blood flow velocity within a living body, said apparatus comprising:

(a) means for selectively exciting nuclei of the body to NMR by applying successive excitation signals within a planar volume which spatially tracks the movements of blood nuclei flowing in a predetermined velocity range; and (b) means for detecting and quantitatively measuring an NMR response signal from nuclei which remain disposed within said planar volume throughout step (a).

30. A non-invasive NMR apparatus as in claim 29, further comprising means for synchronizing each initiation of step (a) with a predetermined time in the pulsatile blood flow cycle of the body.

* * * * *